US012623056B2

(12) United States Patent　(10) Patent No.:　US 12,623,056 B2

Huffer et al.　(45) Date of Patent:　May 12, 2026

(54) SCORING BALLOON CATHETER WITH ENHANCED PUSHABILITY AND MANEUVERABILITY

(71) Applicant: C.R. BARD, INC., Franklin Lakes, NJ (US)

(72) Inventors: Katherine Huffer, Chandler, AZ (US); Mark Nicholas Wright, Gilbert, AZ (US)

(73) Assignee: C.R. BARD, INC., Franklin Lakes, NJ (US)

( * ) Notice: Subject to any disclaimer, the term of this patent is extended or adjusted under 35 U.S.C. 154(b) by 339 days.

(21) Appl. No.: 17/927,887

(22) PCT Filed: Jun. 10, 2020

(86) PCT No.: PCT/US2020/037001

§ 371 (c)(1),
(2) Date: Nov. 27, 2022

(87) PCT Pub. No.: WO2021/251963

PCT Pub. Date: Dec. 16, 2021

(65) Prior Publication Data

US 2023/0201533 A1　　Jun. 29, 2023

(51) Int. Cl.
*A61M 25/01*　　　(2006.01)
*A61B 17/22*　　　(2006.01)

(52) U.S. Cl.
CPC ......... *A61M 25/0138* (2013.01); *A61B 17/22* (2013.01); *A61B 2017/22061* (2013.01)

(58) Field of Classification Search
CPC .......... A61B 17/22; A61B 2017/22038; A61B 2017/22039; A61B 2017/22041;
(Continued)

(56) References Cited

U.S. PATENT DOCUMENTS 6,080,170 A * 6/2000 Nash .............. A61B 17/320758
606/159
6,394,995 B1 5/2002 Solar
(Continued)

FOREIGN PATENT DOCUMENTS

CN　　　103458833 A　　12/2013
CN　　　108289697 A　　7/2018
(Continued)

*Primary Examiner* — Jocelin C Tanner
(74) *Attorney, Agent, or Firm* — Dickinson Wright PLLC; Andrew D. Dorisio; Nicholas P. Coleman

(57)　　　　ABSTRACT

A device for introduction into a body vessel includes a shaft (105), a balloon (115) positioned at the distal end of the shaft (105), and at least one longitudinal scoring wire (135) to score a vascular lesion attached to the distal end of the shaft (105), disposed over the balloon (115). The shaft (105) includes a support (119), such as a wire or tube having one or more spirally cut portions (119A, 119B), which improves pushability and trackability, thereby allowing for use with an external guidewire in a "short rapid exchange" (SRX) format. The balloon (115) expands when fluid is delivered to the balloon (115) through the inflation lumen. This expansion pushes the scoring wire and guidewire against the vascular lesion.

15 Claims, 5 Drawing Sheets

(58) Field of Classification Search
CPC ......... A61B 2017/22061; A61B 2017/320733; A61M 25/0138; A61M 25/104; A61M 2025/018; A61M 2025/109
USPC ......................................................... 606/159
See application file for complete search history.

(56) References Cited

U.S. PATENT DOCUMENTS

| | | | |
|---|---|---|---|
| 2003/0069522 A1 | 4/2003 | Jacobsen et al. | |
| 2004/0092868 A1* | 5/2004 | Murray, III ......... | A61M 25/104 604/103.04 |
| 2005/0154440 A1* | 7/2005 | Limon ................... | A61F 2/958 623/1.11 |
| 2005/0283134 A1* | 12/2005 | Chan ................ | A61M 25/0097 604/523 |
| 2006/0100687 A1 | 5/2006 | Fahey et al. | |
| 2006/0258987 A1 | 11/2006 | Lentz et al. | |
| 2007/0021821 A1* | 1/2007 | Johnson ................. | A61F 2/954 623/1.11 |
| 2007/0135732 A1 | 6/2007 | Dixon et al. | |
| 2008/0147001 A1 | 6/2008 | Al-Marashi et al. | |
| 2008/0171980 A1* | 7/2008 | Hughes ................ | A61M 25/10 604/103.04 |
| 2011/0034989 A1 | 2/2011 | Al-Marashi | |
| 2015/0032027 A1* | 1/2015 | Lupton ................ | A61M 25/09 600/585 |
| 2018/0185051 A1* | 7/2018 | Boyle ........... | A61B 17/320068 |
| 2020/0338318 A1* | 10/2020 | Keary ................... | A61M 25/09 |
| 2021/0307892 A1* | 10/2021 | Walzman ............... | A61B 17/22 |
| 2023/0389955 A1 | 12/2023 | Boyle et al. | |

FOREIGN PATENT DOCUMENTS

| | | |
|---|---|---|
| CN | 109452961 A | 3/2019 |
| CN | 210250850 U | 4/2020 |
| CN | 112218601 A | 1/2021 |
| EP | 3560443 B1 | 3/2021 |
| JP | H0373167 A | 3/1991 |
| JP | H08215312 A | 8/1996 |
| JP | H108533 A | 1/1998 |
| JP | 2018535006 A | 11/2018 |
| WO | 2020032918 A1 | 2/2020 |

* cited by examiner

SCORING BALLOON CATHETER WITH ENHANCED PUSHABILITY AND MANEUVERABILITY

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

Balloon dilatation catheters are used to treat lesions in vessels. However, difficulties are encountered in navigating tortuous anatomy and safely crossing very tight lesions. Moreover, some lesions are difficult to dilate using just a balloon, and require a focused force to dilate the lesion at safe inflation pressures.

U.S. Pat. No. 6,394,995 to Solar et al. describes a system used to provide enhanced force to treat a lesion. This system has a flexible advancement member with a tracking member slidable over a guidewire, and a balloon having a distal end attached to the tracking member. This type of system provides limited focused force, and suffers from a lack of enhanced pushability (e.g, kink resistance) and maneuverability.

SUMMARY OF THE INVENTION

According to an aspect of the disclosure, a balloon catheter is provided with enhanced pushability and maneuverability, by virtue of the omission of an internal guidewire and the inclusion of a support, such as a wire or tube, having one or more spiral cut or spring-like portions.

In one aspect, the disclosure pertains to a balloon catheter having a shaft with a proximal end section, a distal end section, and a support extending from the proximal end section to the distal end section of the shaft. At least a portion of the support comprises a spiral cut portion. A hub is mounted to the proximal end section of the shaft, and an inflatable balloon mounted on the distal end section of the shaft. At least one scoring wire is also provided, the at least one scoring wire having a first end fixed on the shaft between a shaft distal end and the inflatable balloon, a second end connected to the proximal end section of the shaft, and an intermediate portion running alongside of the inflatable balloon.

In one embodiment, the support comprises a tube. The spiral cut portion of the tube may be located within the distal end section of the shaft, within the hub, or both. The support may alternatively comprise a wire, which may also be located within the distal end section of the shaft, the hub, or both.

The balloon catheter may include a spring for connecting the second end of the scoring wire to the proximal end section of the shaft. The at least one scoring wire may comprise two scoring wires, and the shaft may include a lumen for each scoring wire. The distal end section of the shaft includes a guidewire lumen having an inlet distal of the balloon and an outlet distal of the inflatable balloon.

According to a further aspect of the disclosure, a balloon catheter includes a shaft having a proximal end section, a distal end section, and a support extending from the proximal end section to the distal end section, at least a portion of the support comprising a spiral cut portion. A hub is mounted to the proximal end section of the shaft, and an inflatable balloon is mounted on the distal end section of the shaft, the distal end section of the shaft including a guidewire lumen having an inlet distal of the balloon and an outlet distal of the inflatable balloon. At least one scoring wire includes a first end fixed on the shaft between a shaft distal end and the inflatable balloon, a second end connected to the proximal end section of the shaft, and an intermediate portion running alongside of the inflatable balloon.

In one embodiment, the second end of the at least one scoring wire is movably connected to the proximal end section of the shaft. The support may comprise a tube, with the spirally cut portion of the tube is located within the distal end section of the shaft or within the hub (or both). The support may alternatively comprise a wire, which may be similarly located.

Still another aspect of the disclosure relates to a balloon catheter, comprising a shaft having a proximal end section, a distal end section, and a support wire extending from the proximal end section to the distal end section, at least a portion of the support wire comprising a spiral cut portion. A hub is mounted to the proximal end section of the shaft, and an inflatable balloon is mounted on the distal end section of the shaft.

In one embodiment, the balloon catheter includes at least one scoring wire having a first end fixed on the shaft between a shaft distal end and the inflatable balloon, a second end connected to the proximal end section of the shaft, and an intermediate portion running alongside of the inflatable balloon. The second end is movably connected to the proximal end section of the shaft. A spring may also be provided for connecting the second end of the scoring wire to the proximal end section of the shaft. The at least one scoring wire may comprise two scoring wires, and the shaft may includes a lumen for each scoring wire.

In one embodiment, the spirally cut portion of the support wire is located within the distal end section of the shaft. In another embodiment, the spirally cut portion of the support wire is located within the hub. The distal end section of the shaft may include a guidewire lumen having an inlet distal of the inflatable balloon and an outlet distal of the inflatable balloon.

BRIEF DESCRIPTION OF THE DRAWINGS

The above and further advantages of the present invention may be better understood by referring to the following description in conjunction with the accompanying drawings in which.

Figures 1, 1A, 1B:
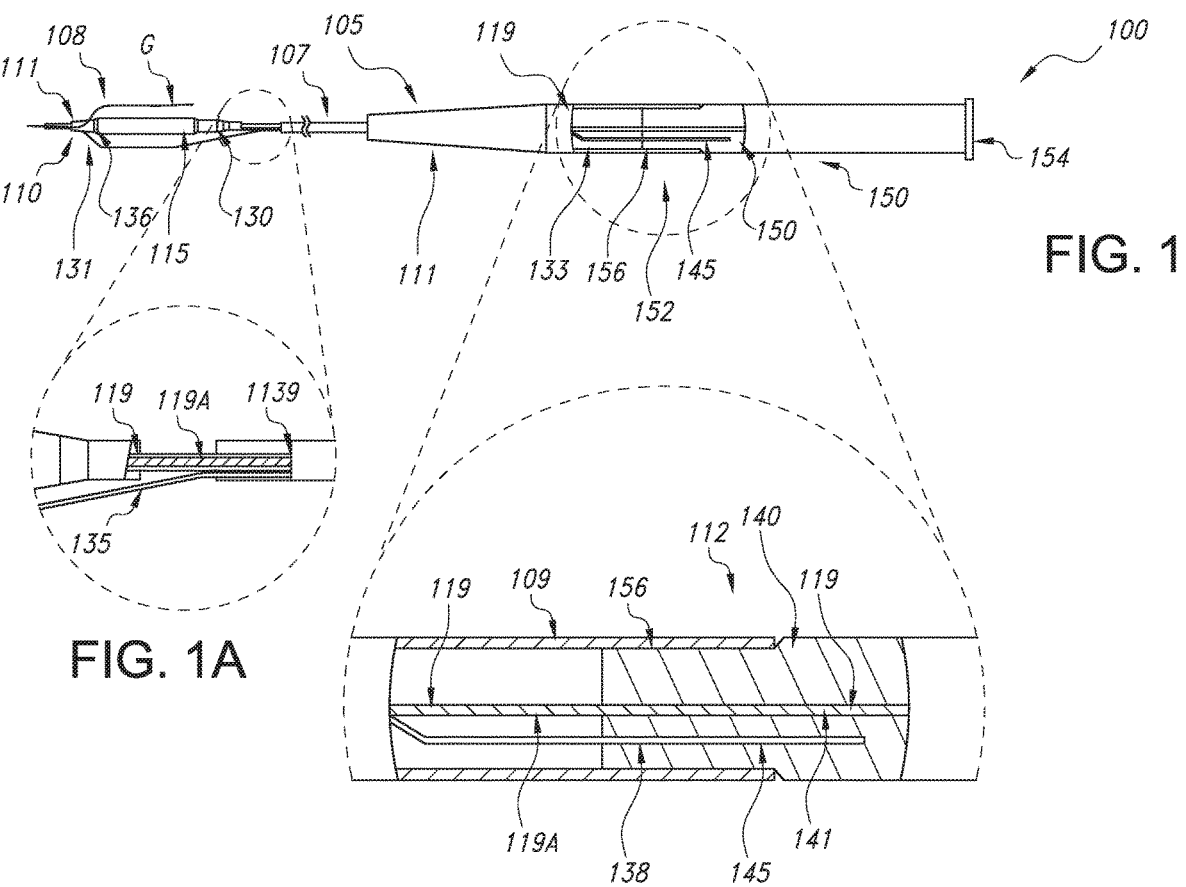
FIG. 1 is a front view of an example of a scoring balloon catheter.
FIG. 1A is a magnified view of the indicated portion of FIG. 1.
FIG. 1B is a magnified view of the indicated portion of FIG. 1.

The dimensions of some of the elements may be exaggerated relative to other elements for clarity or several physical components may be included in one functional block or element. Further, sometimes reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth to provide a thorough understanding of the present invention. The disclosed embodiments may be practiced without these specific details. In other instances, well-known methods, procedures, components, or structures may not have been described in detail so as not to obscure the present invention.

The present disclosure is directed to systems and methods for treatment of a vessel. The principles and operation of systems and methods of the present invention may be better understood with reference to the drawings and accompanying descriptions.

The invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

Certain features of the invention that are, for clarity, described in the context of separate embodiments, may also be provided in combination in a single embodiment. Conversely, various features of the invention that are, for brevity, described in the context of a single embodiment, may also be provided separately or in any suitable sub-combination.

Turning to the invention embodiments, FIG. 1 depicts an embodiment of the invention device. In this invention embodiment, a scoring balloon catheter 100 is shown in a front view with selected sections shown in a magnified view. The catheter 100 comprises comprises a shaft 105 with a shaft proximal section 106 connected to shaft middle section 107 and shaft middle section 107 connected to shaft distal section 108. Shaft tapered section 111 joins shaft proximal section 106 to shaft middle section 107. Shaft 105 also comprises shaft wall 109, which provides a degree of rigidity to shaft 105 such that shaft 105 is suitable for tracking into vasculature or tortuous vasculature being neither too rigid or too flexible. Shaft 105 may comprise a polymeric material, such as Pebax.

In some embodiments, shaft tapered section 111 is fixed to shaft middle section 107. In some embodiments, shaft wall 109 ends before shaft distal end or tip 110 ends. Shaft distal end 110 is the end of shaft 105 that enters the patient first, and may comprise a tip 110 comprising a lumen adapted for receiving a guidewire G. This creates a so-called "short rapid exchange" or "SRX" arrangement, which is one in which the guidewire G runs external to the catheter 100 and thus avoids the need for an internally extending guidewire and the associated complexities that may arise from the same.

The catheter 100 further comprises inflatable balloon 115. Inflatable balloon 115 mounts to shaft 105 along shaft distal section 108. In some embodiments, inflatable balloon 115 ends to shaft distal end 110. In these or other embodiments, inflatable balloon 115 is fixed to shaft 105.

Inflatable balloon 115 comprises inflatable balloon proximal end 130 and distal end 131. A typical embodiment has a flexible, polymeric film serving as inflatable balloon 115 and having an outer surface 132. For this disclosure, inflatable balloon proximal end 130 is the portion of inflatable balloon 115 that attaches or fixes the proximal end of inflatable balloon 115 to shaft 105. Inflatable balloon proximal end 130 is defined as the proximal portion of inflatable balloon 115 that remains contacting shaft 105 after inflatable balloon 115 is inflated.

For this disclosure, inflatable balloon distal end 131 is the portion of inflatable balloon 115 that distally attaches or fixes inflatable balloon 115 to shaft 105. Inflatable balloon distal end 131 is defined as the distal portion of inflatable balloon 115 that remains contacting shaft 105 after inflatable balloon 115 in inflated. An inflation lumen 133 fluidly communicates with inflatable balloon 115, which allows inflatable balloon 115 to be inflated by fluid passing therethrough.

Catheter 100 further comprises hub 140. Hub 140 resides inside of shaft 105 within shaft proximal section 106. Hub 140 comprises a passage 141 for the support 119 to pass through. Hub 140 further comprises one or more hub lumens 145.

Catheter 100 further comprises a support 119, which may take the form of a solid wire or hollow tube (such as, for example, a hypotube) and may be made of a metal (such as, for example, stainless steel gold, silver, platinum, titanium, or any other biocompatible metal or like material). The support 119 may extend longitudinally from at least from shaft proximal end 112, such as from within hub 140, to adjacent the shaft distal end or tip 110. At least a portion of the support 119, such as the portion located within the hub 140, may be functionally modified to provide enhanced flexibility. This may be achieved by providing this portion of the support 119 with a spiral cut portion 119A, as indicated in FIG. 1A. This spiral cut portion 119A may be achieved, for example, by laser cutting, and essentially creates a spring-like portion of the support 119. This helps to provide shaft 105 with sufficient rigidity in view of the lack of an internal guidewire, and thus improves trackability of the catheter 100, while maintaining a high degree of pushability. As a result of the expandability provided, this feature also helps to avoid kinking, especially when the balloon is inflated and the shaft 105 diameter grows as a result.

Catheter 100 may further comprise one or more scoring wires 135, with only one such wire shown in the embodiment of FIGS. 1, 1A, and 1B running alongside of balloon 115 (with the guidewire G also extending alongside balloon so as to provide a scoring function). This scoring wire 135 may have a fixed end 136, a section 137 extending alongside the balloon, and a movable end 138. Fixed end 136 connects within shaft distal section 108 distal of the inflatable balloon distal end 131. In some embodiments, fixed end 136 attaches to the outer side of shaft wall 109. Fixed end 136 may be attached using any method known to those of ordinary skill in the art. This configuration provides for a focused force element (scoring wire 135) alongside inflatable balloon 115.

The distance between scoring wire 135 and outer surface 132 can be any value recognized as useful by those of ordinary skill in the art. Once past inflatable balloon 115, scoring wire 135 may extend below shaft wall 109 and proximally inside of shaft 105. Movable end 138 sits inside of shaft 105 within shaft proximal section 106. In some embodiments, scoring wire 135 occupies at least part of lumen 1139 (see FIGS. 6A and 6B).

FIGS. 1, 1A, and 1B depict catheter 100 as having two scoring wires, one of which is translatable scoring wire 135, and the other of which is guidewire G. In some embodiments, catheter 100 has 1-15, 3-10, or 2-5 scoring wires. In some embodiments the diameter of scoring wire 135 is between 0.003 inches and 0.040 inches, or 0.005 inches and 0.015 inches, 0.008 inches and 0.012 inches. In some embodiments, scoring wire 135 is 0.10 inches. Scoring wire 135 need not have a uniform diameter, and may have a larger diameter at a distal end as compared to a proximal end. In some embodiments, scoring wire 135 comprises metals, metal alloys, polymers, and shape memory materials that are metal-based or polymer-based.

In some embodiments, the interaction encompasses movable scoring wire end 138 connected in or to hub lumen 145. In some embodiments, movable scoring wire end 138 is fixed to hub lumen 145. In other embodiments, the interaction encompasses movable scoring wire end 138 being slidably engaged inside of hub lumen 145. In some embodiments hub 140 comprises any biocompatible material such as metals, metal alloys, and polymers. In some embodiments hub 140 comprises nylon, Pebax, or any other suitable material.

In some embodiments hub 140 is substantially fixed inside shaft proximal section 106 with movable scoring wire end 138 slidably engaged or disposed within hub lumen 145. In some embodiments, hub 140 is longitudinally movable or elastic, allowing movable scoring wire end 138 to move longitudinally by pulling hub 140 distally, by moving hub 140 or by stretching material of hub 140. For instance, in some embodiments, hub 140 is elastic. When movable scoring wire end 138 is subjected to a distally directed force that causes it to move distally and when movable scoring wire end 138 is fixed to or within hub lumen 145, the movement stretches hub 140. The restoring force or force counter to that distal stretching (counterforce) tends to move movable scoring wire end 138 substantially back into place when the distally directed force is removed.

Scoring wire catheter 100 may further comprises handle assembly 150. Handle assembly 150 associates with shaft proximal end 109. Handle assembly 150 may comprise a transition subassembly 152 including a stepped-down portion 156, in which the overall outside dimension has a step transition decreasing to a smaller diameter, sized to engage shaft proximal end 112. In some embodiments, transition subassembly 152 does not have stepped-down portion 156.

Shaft 105 relates to handle assembly 150 through shaft proximal end 112 and stepped-down portion 156. In some embodiments, shaft 105 connects to handle assembly 150. For example, shaft proximal end 112 can slide over stepped-down portion 156 and the components can be fixed such as by welding, fusing, gluing, etc. The friction fit between shaft proximal end 112 and transition sub-assembly 152 can be strong enough to fix the components together. In some embodiments lacking stepped-down portion 156, shaft proximal end 112 can connect to handle assembly 150 through a butt joint between shaft proximal end 112 and transition subassembly 152.

The handle assembly 150 may comprise a port 154. This port 154 carries gas or inflation fluid into inflatable balloon 115 via a lumen 120 to inflate it or carries gas or inflation fluid out of inflatable balloon 115 to deflate it.

Operationally, in the devices taught by the FIG. 1 embodiment, for treatment of calcified lesions, for example, a physician cuts through the patient's tissue until an appropriately sized vessel is revealed. The vessel must lead to the lesion site following a path that catheter 100 can follow. In some embodiments, the location of the lesion site may result in the selection of a more or less flexible shaft 105 or catheter 100.

The physician opens the vessel, inserts a guidewire into the vessel, and advances the guidewire through the patient's vasculature under ultrasound, magnetic resonance, fluoroscopic, or some other type of guidance. Once the physician places the guidewire G at a satisfactory site, the physician threads the proximal end of the guidewire into the distal guidewire lumen associated with tip 110, the entrance and exit of which lumen are distal of the balloon 115. With the guidewire G in place and connected to catheter 100, the physician maneuvers the catheter 100 along the guidewire G until inflatable balloon 115 reaches the desired position near the lesion site. Typically, this position will allow at least one scoring wire 135 to effectively engage the lesion. After that, the physician inflates inflatable balloon 115 until scoring wire 135 firmly presses into or cracks the lesion. Once lesion treatment with catheter 100 is complete, the physician deflates inflatable balloon 115, which allows scoring wire 135 to relax away from the lesion and from the vessel wall.

Scoring wire 135 contacts the lesion as long as inflatable balloon 115 remains inflated. The inflation time corresponds to the time the physician chooses for scoring wire 135 to contact the lesion. Inflation times may range from 5 seconds to 5 minutes. The nature of the lesion may determine the appropriate inflation time and inflation speed.

As inflatable balloon 115 inflates, scoring wire (or wires) 135 expands outwardly, placing scoring wire 135 under longitudinal tension. A component of the force vector caused by that longitudinal tension points proximally from fixed end 136 and distally from movable end 138. Therefore, any movement of scoring wire 135 occurs at movable end 138. Hub 140 constrains the movement of movable end 138 allowing it to move longitudinally. This movement decreases the strain on inflatable balloon 115 helping to maintain its engineered shape and helping to avoid any kinking.

When the physician deflates the balloon 115, the forces previously causing scoring wire 135 to expand disappear, allowing scoring wire 135 (and movable end 138) to relax. Hub 140 constrains the relaxation of movable end 138. Specifically, hub 140 guides movable end 138 into an arrangement similar to the initial arrangement of movable end 138 before balloon inflation. The action of hub 140 helps regularize the inflation and deflation steps increasing their predictability.

FIG. 1A is magnified view of shaft proximal section 106. Shaft 105 ends at shaft proximal end 112 and receives hub 140, which is either part of distal end 155 or not. Hub 140 can have one or more hub lumens 145—FIG. 1A shows hub lumen 145. The hub lumen 145 extends into hub 140 longitudinally in this embodiment. Catheter 100 does not need lengthwise hub lumen 145 to function correctly. Hub lumen 145 need only functions to slidably and reversibly receive movable end 138. FIG. 1A shows hub lumen 145 extending into hub 140 approximately three quarters of the length of hub 140, but this is not critical. In some embodiments, hub lumen 145 extends completely through hub 140. Hub lumen 145 extends into hub 140 as far as or further than movable end 138 extends into hub lumen 145.

FIG. 1A also shows scoring wire 135 and movable end 138. In this embodiment, scoring wire 135 tapers or flares outwardly after proximally exiting lumen 1139. Movable end 138 occupies a portion of hub lumen 145. In this embodiment, catheter 100 comprises one hub lumen 145 per movable end 138, in case more than one scoring wire is present. Other embodiments exist in which a hub lumen can interact with more than one movable end 138.

FIG. 1B depicts a magnified view of the region where scoring wire 135 distally exits lumen 1139. Scoring wire 135 has a path through part of catheter 100. Lumen 1139 is a lumen that receives scoring wire 135 along some or all of shaft middle section 107. After exiting, scoring wire 135 flares outward as it progresses distally, extending in a substantially longitudinal direction until the wire is past the balloon distal end 131. At that point scoring wire 135 turns inwardly until it reaches shaft distal section 108. The scoring wire fixed end 136 attaches to catheter 100 distally of inflatable balloon 115 or at or near the point where balloon distal end 131 attaches to catheter 100. The portion of scoring wire 135 within section 137 has a longitudinal region along inflatable balloon 115.

In the operation of the group of embodiments represented by the device in FIG. 1, a physician places inflatable balloon 115 as described above. The physician inflates inflatable balloon 115 through lumen port 154. Balloon inflation first applies outward pressure on scoring wire 135 and guidewire G and forces the same to engage the lesion. Without wishing to be bound by any particular theory of operation, it is believed that, because movable end 138 is moveably connected, scoring wire 135 does not contribute to balloon or balloon deformation caused by inflation or overinflation. Since this wire 135 and guidewire G can move outwardly, their presence does not significantly cage the balloon, which prevents the balloon 115 from expanding past the wires. If inflation continues, some other portion of the balloon 115 will deform from the pressure exerted by the inflation fluid. In some cases, balloon deformation leads to problems with later deflating the balloon. Instead, the outwardly directed inflation pressure on scoring wire 135 causes movable end 138 to move distally, which lowers the counterforce that scoring wire 135 exerts against inflatable balloon 115. As movable end 138 moves distally, it recedes from hub lumen 145. In some embodiments, inflation pressure causes movable end 138 to pull out of hub lumen 145. In other embodiments, movable end 138 remains inside of hub lumen 145.

The physician maintains pressure in inflatable balloon 115 long enough for scoring wire 135 to have the desired effect. Afterward, the physician releases pressure, inflatable balloon 115 deflates, and movable end 138 re-extends into hub lumen 145.

Figures 2, 2A, 2B:
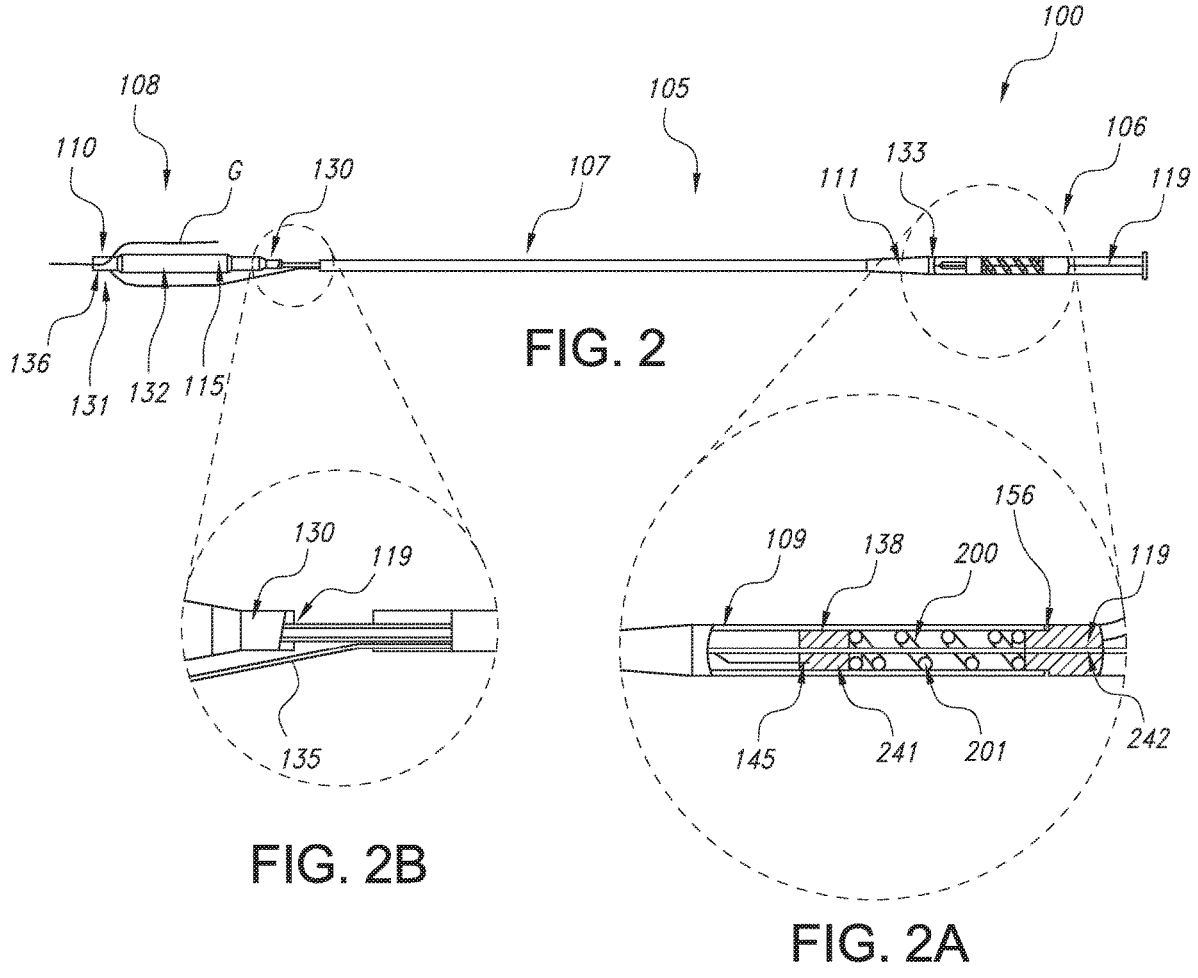
FIG. 2 is a front view of another example of an invention device.
FIG. 2A is a magnified view of the indicated portion of FIG. 2.
FIG. 2B is a magnified view of the indicated portion of FIG. 2.

FIGS. 2, 2A, and 2B depict a different embodiment of a scoring balloon catheter 100, the main difference being the hub and the proximal scoring wire geometry. FIG. 2B depicts a hub 140 that has hub distal section 241 and hub proximal section 242. Hub proximal section 242 through stepped-down portion 156 serves to connect shaft 105 with handle assembly 150. Additionally, hub proximal section 242 serves as a stop for a spring 200. Spring 200 comprises spring wire 201, which adds resilience to the mechanism of scoring wire 135.

Hub distal section 241 lies next to the distal end of spring 200. Hub distal section 241 connects (attaches) to movable end 138. In some embodiments, hub distal section 241 is fixed to movable end 138. In other embodiments, hub distal section 241 comprises hub lumen 145, which may be fixed to movable end 138. Movable end 138 flares outwardly as it reaches hub distal section 241. A guidewire G also extends through a guidewire lumen in the tip 110, which is distal of the balloon distal end 131

As in the above embodiment, as inflatable balloon 115 inflates, the counterforce that scoring wire 135 would otherwise apply, is moderated by movable end 138. Movable end 138 moves distally as before, but hub distal section 241 also moves distally. The arrangement of hub distal section 241, spring 200, and hub proximal section 242 imparts force, through hub distal section 241, to movable end 138. This force tends to proximally bias movable end 138. And when the physician deflates the balloon as before, movable end 138 moves proximally, substantially back to its initial position, aided by the force of spring 200.

Figures 3, 4, 4A:
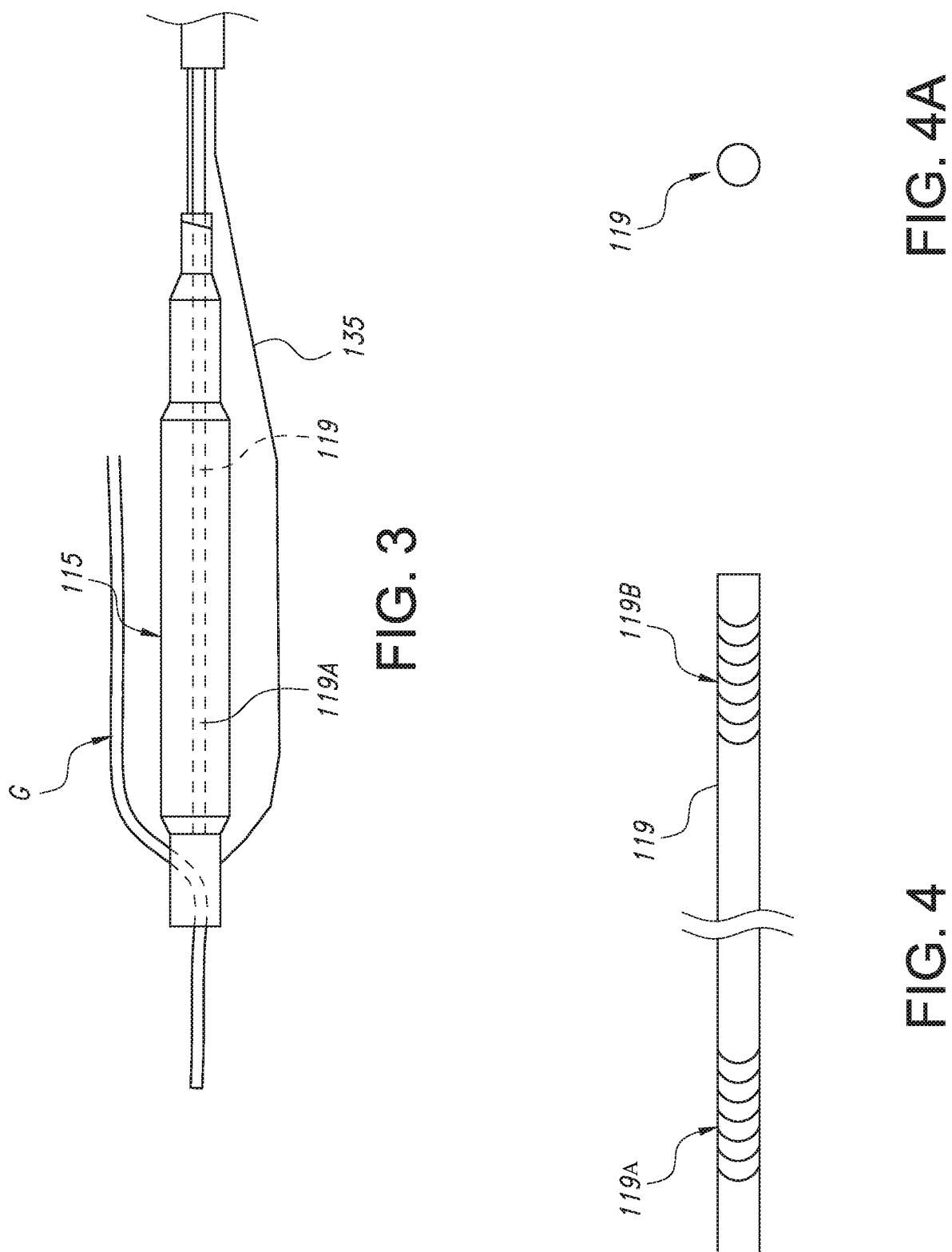
FIG. 3 is a magnified view of a distal end of a scoring balloon catheter according to one aspect of the disclosure.
FIG. 4 is a view of a support for the catheter.
FIG. 4A is a first cross-sectional view of the support.

FIG. 3 discloses an embodiment of the distal section of the catheter 100. As indicated, the support 119 may extend the entire length of the balloon 115 to the tip 110 of the catheter 100. This figure further shows that the portion of the support 119 extending along the balloon 115 may be functionally modified as noted above, such as by being formed of a spiral cut wire or tube, thus creating a spring-like portion. Again, this helps to provide shaft 105 with sufficient rigidity in view of the lack of an internal guidewire, and thus improves trackability of the catheter 100, while maintaining a high degree of pushability.

FIG. 4 illustrates that the support 119 may comprise an elongated wire having a spiral cut portion 119A. While shown at the distal end, it can be appreciated that it may be located elsewhere, such as at the proximal end. More than one spiral cut portion, such as portion 119B, may also be provided. It can also be understood from FIG. 4 that the support 119 may have a length L, which may be at least as great as the distance D from the distal tip 110 of the catheter to the proximal end of the hub 140, as indicated in FIG. 1. FIG. 4A also shows that the support 119 when in the form of a wire has a solid cross-sectional area, save for the spiral cut portion 119A, but as noted above, the support may also comprise a hollow tube. In any case, the resulting portion 119A, 119B is spring-like and flexible as a result of being spirally cut as proposed.

Figures 5A, 5B:
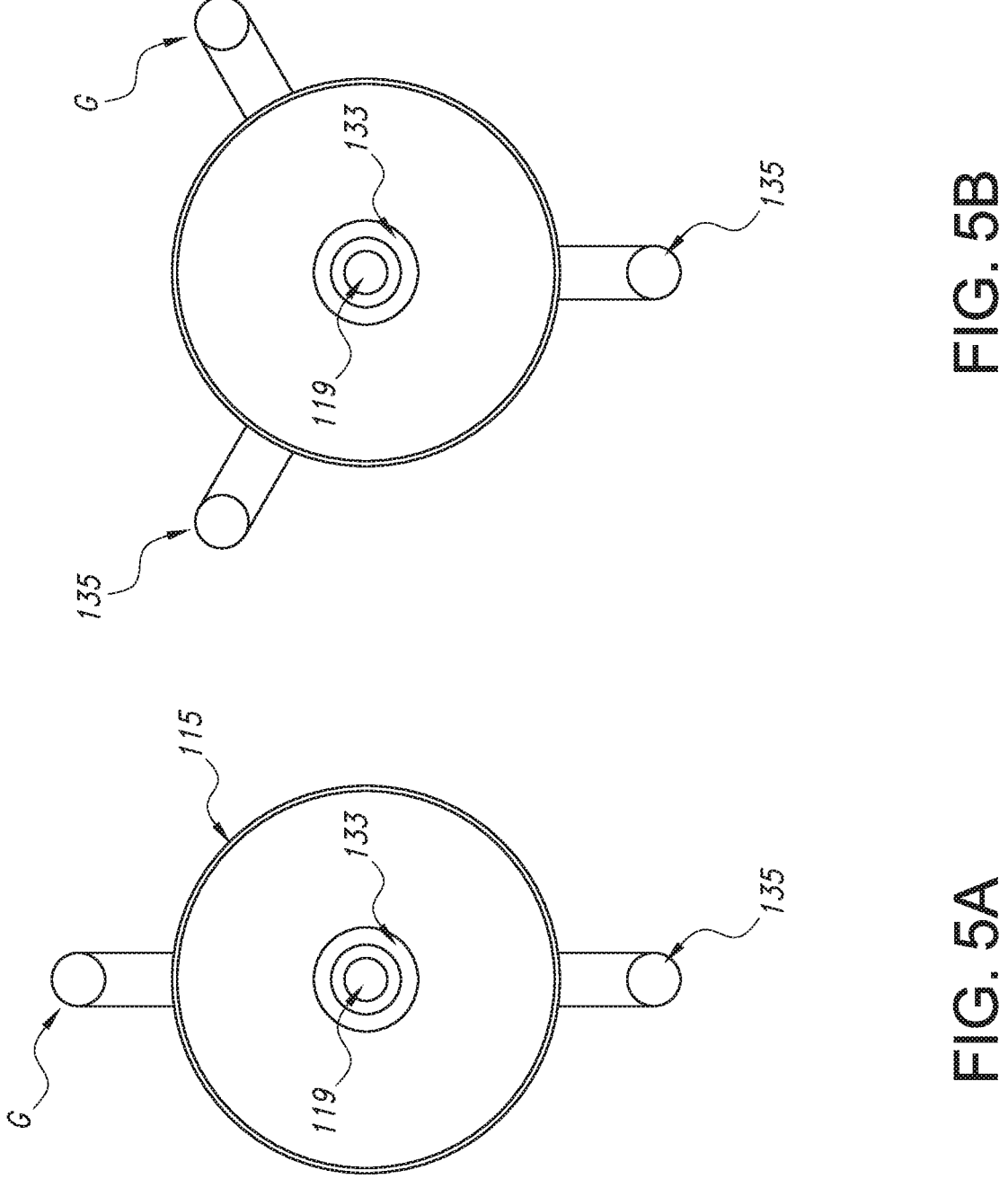
FIG. 5A is an end view showing the embodiment of FIG. 1 at section plane BB.
FIG. 5B is similar to FIG. 5A viewing section on a different invention embodiment.

FIG. 5A depicts section BB of FIG. 1. It shows scoring wire 135, guidewire G, inflatable balloon 115, inflation lumen 133, and support 119. As can be seen, section plane BB cuts through catheter 100 at shaft distal section 108. The plane also cuts inflatable balloon 115; cuts scoring wire 135 at balloon section 137 showing cross-section 505. FIG. 5B depicts a similar embodiment, but with two scoring wires 135 present, as well as guidewire G which may also provide scoring functionality.

Figure 6A:
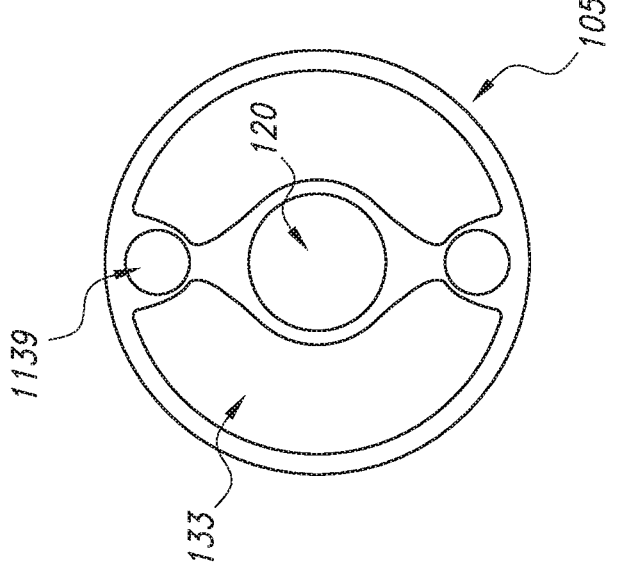
FIG. 6A is a sectional view showing an embodiment of the device taken along a section plane similar to section plane AA of FIG. 1.

FIG. 6A depicts section AA of FIG. 1. It shows two lumens 1139 in shaft 105 sitting side-by-side for receiving the scoring wires (not shown) if two are present. It also shows inflation lumen 133 and lumen 120 for receiving support 119 (wire or rod). Lumen 1139 need not adopt a side-by-side configuration, as shown in this figure, but can adopt a configuration distributed around the perimeter of shaft 105. A single lumen 1139 may also be provided.

Figure 6B:
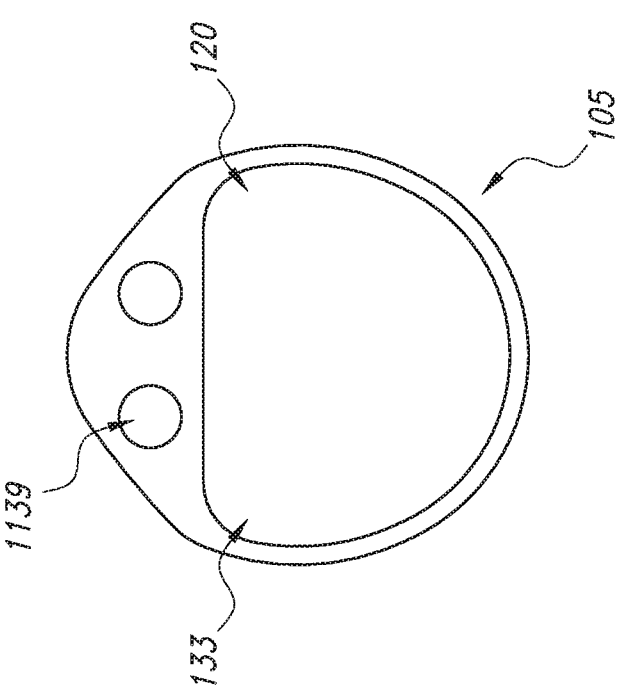
FIG. 6B is similar to FIG. 6A viewing section plane AA on a different invention embodiment.

FIG. 6B shows a different embodiment with two lumens 1139, each for receiving a scoring wire (not shown) distributed across from each other in shaft 105. This distribution need not be symmetric and, only one scoring wire may be present, in which case only one such lumen would be needed. Also in this figure, a lumen 120 for support lies within shaft 105, and is coaxial with dual inflation lumens 133.

In any of the embodiments set out above, inflatable balloon 115 can have any of a variety of diameters ranging from 1.25-40 mm or 2.0-8.0 mm. In any of the embodiments set out above, inflatable balloon 115 can have any of a variety of lengths such as 10-300 mm or 20-300 mm. Long balloons may be particularly useful for treating peripheral lesions, which often have long diseased portions.

While it is preferred to include a scoring wire, it can also be appreciated that the catheter 100 may be useful without the same, such as by providing angioplasty without cutting or scoring the lesion. In such an embodiment, the support 119 with one or more spiral cut portions 119A, whether in the form of a tube or wire, may extend the entire length of the shaft 105, such as from the proximal end section to the distal end section of catheter 100, including the balloon 115.

Summarizing, this disclosure may be considered to relate to the following items:

1. A balloon catheter, comprising:
   a shaft having a proximal end section, a distal end section, and a support extending from the proximal end section to the distal end section of the shaft, at least a portion of the support comprising a spiral cut and/or spring-like portion;
   a hub mounted to the proximal end section of the shaft;
   an inflatable balloon mounted on the distal end section of the shaft; and
   at least one scoring wire having a first end fixed on the shaft between a shaft distal end and the inflatable balloon, a second end connected to the proximal end section of the shaft, and an intermediate portion running alongside of the inflatable balloon.

2. The balloon catheter of item 1, wherein the support comprises a tube.

3. The balloon catheter of item 2, wherein the spiral cut and/or spring-like portion of the tube is located within the distal end section of the shaft.

4. The balloon catheter of item 2, wherein the spiral cut and/or spring-like portion of the tube is located within the hub.

5. The balloon catheter of item 1, wherein the support comprises a wire.

6. The balloon catheter of item 5, wherein the spiral cut and/or spring-like portion of the wire is located within the distal end section of the shaft.

7. The balloon catheter of item 5, wherein the spiral cut and/or spring-like portion of the wire is located within the hub.

8. The balloon catheter of any of items 1-7, further including a spring for connecting the second end of the scoring wire to the proximal end section of the shaft.

9. The balloon catheter of any of items 1-8, wherein the at least one scoring wire comprises two scoring wires, and optionally the shaft includes a lumen for each scoring wire.

10. The balloon catheter of any of items 1-9, wherein the distal end section of the shaft includes a guidewire lumen having an inlet distal of the balloon and an outlet distal of the inflatable balloon.

11. The balloon catheter of item 10, further including a guidewire extending through the guidewire lumen and including a portion running alongside the balloon.

12. A balloon catheter, comprising:
   a shaft having a proximal end section, a distal end section, and a support extending from the proximal end section to the distal end section, at least a portion of the support comprising a spiral cut and/or spring-like portion;
   a hub mounted to the proximal end section of the shaft;
   an inflatable balloon mounted on the distal end section of the shaft, the distal end section of the shaft including a guidewire lumen having an inlet distal of the balloon and an outlet distal of the inflatable balloon; and
   at least one scoring wire having a first end fixed on the shaft between a shaft distal end and the inflatable balloon, a second end connected to the proximal end section of the shaft, and an intermediate portion running alongside of the inflatable balloon.

13. The balloon catheter of item 12, wherein the second end of the at least one scoring wire is movably connected to the proximal end section of the shaft.

14. The balloon catheter of item 12 or item 13, wherein the support comprises a tube.

15. The balloon catheter of item 14, wherein the spirally cut portion of the tube is located within the distal end section of the shaft.

16. The balloon catheter of item 43, wherein the spirally cut portion of the tube is located within the hub.

17. The balloon catheter of item 12 or item 13, wherein the support comprises a wire.

18. The balloon catheter of item 17, wherein the spirally cut portion of the wire is located within the distal end section of the shaft.

19. The balloon catheter of item 17, wherein the spirally cut portion of the wire is located within the hub.

20. The balloon catheter of any of the preceding items 12 to 19, further including a guidewire extending through the guidewire lumen and including a portion running alongside the balloon.

21. A balloon catheter, comprising:
   a shaft having a proximal end section, a distal end section, and a support wire extending from the proximal end section to the distal end section, at least a portion of the support wire comprising a spiral cut and/or spring-like portion;
   a hub mounted to the proximal end section of the shaft; and
   an inflatable balloon mounted on the distal end section of the shaft.

22. The balloon catheter according to item 21, further including at least one scoring wire having a first end fixed on the shaft between a shaft distal end and the inflatable balloon, a second end connected to the proximal end section of the shaft, and an intermediate portion running alongside of the inflatable balloon.

23. The balloon catheter according to item 21, wherein the second end is movably connected to the proximal end section of the shaft.

24. The balloon catheter according to item 21 or item 22, further including a spring for connecting the second end of the scoring wire to the proximal end section of the shaft.

25. The balloon catheter of any of items 21-24 wherein the at least one scoring wire comprises two scoring wires, and the shaft optionally includes a lumen for each scoring wire.

26. The balloon catheter of any of items 21-25, wherein the spiral cut and/or spring-like portion of the support wire is located within the distal end section of the shaft.

27. The balloon catheter of any of items 21-25, wherein the spiral cut and/or spring-like portion of the support wire is located within the hub.

28. The balloon catheter of any of the preceding items 21 to 27, wherein the distal end section of the shaft includes a guidewire lumen having an inlet distal of the inflatable balloon and an outlet distal of the inflatable balloon.

29. The balloon catheter of item 28, further including a guidewire extending through the guidewire lumen and including a portion running alongside the balloon.

Although the invention has been described in conjunction with specific embodiments, many alternatives, modifications, and variations will be apparent to those skilled in the art. Accordingly, it embraces all such alternatives, modifications, and variations that fall within the appended claims' spirit and scope. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A balloon catheter, comprising:
a shaft having a proximal end section, a distal end section, and a support extending from the proximal end section to the distal end section of the shaft, at least a portion of the support comprising a solid wire with spiral cut portion;
a hub mounted to the proximal end section of the shaft;
an inflatable balloon mounted on the distal end section of the shaft, wherein at least a portion of the support positioned within the shaft between the proximal end section and the inflatable balloon; and
at least one scoring wire having a first end fixed on the shaft between a shaft distal end and the inflatable balloon, a second end connected to the proximal end section of the shaft, and an intermediate portion running alongside of the inflatable balloon;
wherein the distal end section of the shaft includes a guidewire lumen having an inlet distal of the balloon and an outlet distal of the inflatable balloon.

2. The balloon catheter of claim 1, wherein the spiral cut portion of the wire is located within the distal end section of the shaft.

3. The balloon catheter of claim 1, wherein the spiral cut portion of the wire is located within the hub.

4. The balloon catheter of claim 1, further including a spring for connecting the second end of the scoring wire to the proximal end section of the shaft.

5. The balloon catheter of claim 1 wherein the at least one scoring wire comprises two scoring wires, and the shaft includes a lumen for each scoring wire.

6. The balloon catheter of claim 1, further including a guidewire extending through the guidewire lumen and including a portion running alongside the balloon.

7. A balloon catheter, comprising:
a shaft having a proximal end section, a distal end section, and a support extending from the proximal end section to the distal end section, at least a portion of the support comprising a solid wire with a spiral cut portion;
a hub mounted to the proximal end section of the shaft;
an inflatable balloon mounted on the distal end section of the shaft, the distal end section of the shaft including a guidewire lumen having an inlet distal of the balloon and an outlet distal of the inflatable balloon;
a guidewire adapted to pass through a lumen in a distal tip of the shaft; and
at least one scoring wire having a first end fixed on the shaft between a shaft distal end and the inflatable balloon, a second end connected to the proximal end section of the shaft, and an intermediate portion running alongside of the inflatable balloon.

8. A balloon catheter, comprising:
a shaft having a proximal end section, a distal end section, and a solid support wire extending at least partially within the shaft from the proximal end section to the distal end section, at least a portion of the solid support wire comprising a spiral cut portion;
a hub mounted to the proximal end section of the shaft;
an inflatable balloon mounted on the distal end section of the shaft; and
a guidewire lumen having an inlet distal of the inflatable balloon and an outlet distal of the inflatable balloon.

9. The balloon catheter according to claim 8, further including at least one scoring wire having a first end fixed on the shaft between a shaft distal end and the inflatable balloon, a second end connected to the proximal end section of the shaft, and an intermediate portion running alongside of the inflatable balloon.

10. The balloon catheter according to claim 9, wherein the second end is movably connected to the proximal end section of the shaft.

11. The balloon catheter according to claim 10, further including a spring for connecting the second end of the scoring wire to the proximal end section of the shaft.

12. The balloon catheter of claim 8 wherein the at least one scoring wire comprises two scoring wires, and the shaft includes a lumen for each scoring wire.

13. The balloon catheter of claim 8, wherein the spiral cut portion of the support wire is located within the distal end section of the shaft.

14. The balloon catheter of claim 8, wherein the spiral cut portion of the support wire is located within the hub.

15. The balloon catheter of claim 8, further including a guidewire extending through the guidewire lumen and including a portion running alongside the balloon.

* * * * *